United States Patent [19]

Miller

[11] 3,997,296
[45] Dec. 14, 1976

[54] PRIMARY STANDARDS
[75] Inventor: Warren V. Miller, Newton, N.J.
[73] Assignee: Spex Industries Inc.
[22] Filed: Feb. 6, 1975
[21] Appl. No.: 547,605
[52] U.S. Cl. .......................................... 23/232 R
[51] Int. Cl.² ........................................ G01N 1/00
[58] Field of Search ................................ 23/232 R
[56] References Cited
UNITED STATES PATENTS

| | | | |
|---|---|---|---|
| 1,321,062 | 11/1919 | Lamb et al. | 23/232 R |
| 3,119,670 | 1/1964 | Mitchell et al. | 23/232 R |
| 3,847,551 | 11/1974 | Hutson | 23/232 R |

OTHER PUBLICATIONS

Central Scientific Co., Catalog J–300, 1962, p. 127.
Aloe Scientific Co., Catalog 103, 1952, pp. 1010, 1011.
Vaska, L., Science 140, 809 (1963).

*Primary Examiner*—Robert M. Reese
*Attorney, Agent, or Firm*—C. Walter Mortenson

[57] ABSTRACT

Apparatus is supplied for providing a primary standard of a gas by sealing in a container a material which is the source of the gas in predetermined amounts. Upon releasing the gas from the material, sample aliquots are removed and are passed into the analytical equipment being used in the subject testing.

15 Claims, 1 Drawing Figure

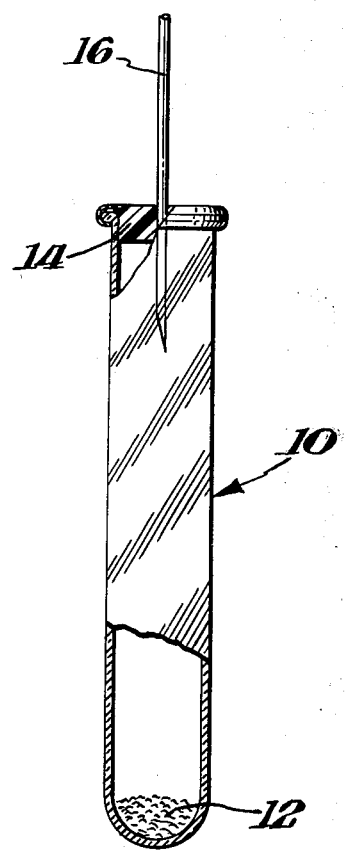

PRIMARY STANDARDS

BACKGROUND OF THE INVENTION

This invention relates to the provision of standards that can be readily and reliably used in analyses, one important application being the anaylsis of air pollutants. With increasing population, pollution problems increase, it seems, exponentially rather than linearly. Thus, vastly improved methods for analyzing impurities in the atmosphere are urgently needed.

There are, of course, many efficient analytic methods and apparatus such as gas chromatography, infra-red, among other techniques. In present methods for preparing gas standards for use in air pollution analyses one employs precision flow systems, permeation tubes, gas mixtures contained in metal cylinders or spray cans and the pyrolysis lf organic material at high temperatures using a carrier gas stream. However, disadvantages exists in the present approaches. For example, the flow dilution method requires the use of extensive gas flow trains in order to reduce gas concentration to a low level. Permeation tubes require individual calibration, and the rate of gas diffusion through the tube is very sensitive to temperature changes. While the spray can or cylinder standards are convenient, the gas or gases therein can react with or adsorb on cylinder walls over extended time periods. The pyrolysis technique is accurate under controlled conditions, but presently this approach is limited to sulfur dioxide, and analysis is difficult because certain detectors do not give reliable results if sulfur compounds other than sulfur dioxide are present, for example, inadvertently due to imcomplete pyrolysis.

Thus, an object of this invention is to provide methods and materials for primary standardization which avoid certain existing problems in the analytic field. Another purpose is the provision of readily portable standards which can be prepared easily just before use and which afford a wide variety of test conditions. A still further aim is the provision of materials and methods for readily custom-building a tandard for use in a given situation, including immediate, on-location testing. These and other objectives will appear hereinafter.

DESCRIPTION OF THE PRIOR ART

As discussed briefly above, prior art methods and procedures usually employ elaborate equipment or involve temperature effects that are either not readily controlled or involve the production of multiple gases. Thus, there has been heretofore no simple method or equipment for use in air pollution analyses. As will be seen below, this invention affords many advantages over the prior art. One can readily produce a given, desired concentration of a gas in a repeared, precise fashion and use it as a standard in the same equipment that is being used to analyze the suspected air.

DESCRIPTION OF THE INVENTION AND PREFERRED EMBODIMENTS

As indicated above, this invention involves preparing a substance which is a source of the gas and from which the gas can be readily released. The amount of the gas obtainable from a known amount of the substance is fixed and is readily calculated. Therefore, an open container, such as a piece of glass tubing that can be sealed can be made to contain an accurately weighed amount of the substance and the container can be sealed with said known amount of said substance in it. When ready for use, the gas may be readily dissociated from said substance, as by heating it to the dissociation temperature, and the tube may be opened while it is in conduit relationship with the analytical equipment which is being used or if it is sealed with a serum cap, aliquots may be withdrawn. Thus, the entire, or a part of the entire, yet precisely known amount of gas is passed directly into the said equipment and a reading is easily obtained for direct comparison from a reading prevously or about to be obtained using a sample of air or atmosphere being tested for pollution.

In the process and apparatus (shown in the drawing, a front elevation partly broken away) of this invention gasreleasable substances such as transition metal complexes and clathrates are used. The complexes react reversibly with various gases such as the nitrogen oxides, carbon monoxide and sulfur dioxide forming adducts with known stoichiometry. Thus, a known amount of gas associated with the complex can be readily released from the complex. Similarly, inorganic clathrates can be prepared to contain a known amount of a given gas. Clathrates are latticed materials and gases can be entrapped in the interstices and kept there until released again, as by heating. A known weight of the clathrate can be made to contain a known weight of a given gas. Thus, upon being made to dissociate in a sealed container of known volume, the gas standard is obtained, being an exact amount of gas per unit volume based on the weight of material used.

Particularly useful are transition metal complexes such as chlorocarbonylbis(triphenylphosphine)iridium(1) and bis(1,2-diphenylphosphinoethane)iridium(1) and clathrates such as dicyanomonoaminenickel(11) benzene clathrate and beta-quinol hydrogen sulfide clathrates. Thus, in the practice of this invention as iridium complex is formed as by the following reaction with sulfur dioxide ($SO_2$) as the gas:

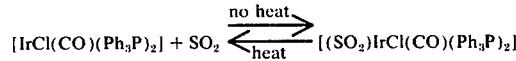

wherein $Ph_3P$ is triphenylphosphine. Similar equations can be written for other gaseous molecules as carbon monoxide, hydrogen halides, such as hydrogen chloride, hydrogen, oxygen, among others. As an example of a clathrate use, the following equation is illustrative:

in which benzene ($C_6H_6$) is released from the latticed dicyanomonoaminenickel (11) on gentle heating. The benzene can be replaced by toluene or any of the xuylenes as well. Included in the term "gas-releasable substance" are thermally unstable salts which are not complexes or clathrates, but which can be decomposed easily by the application of heat to release only one gas. Such salts include silver nitrite, mercuric cyanide, potassiumhexachloropalladate, cesium dibromochloride, and potassium hydrogen fluoride, among others.

In the figure, 10 represents the container for the apparatus of this invention which contains the material 12 which is the source of gas. As shown, the container is sealed at 14, as for example, with a septum cap, and gas-tight syringe 16 can be used for withdrawing aliquots from the container.

This invention may be further understood by reference to the following examples which are given for illustrative purposes only and in which parts and percentages are by weight unless otherwise indicated:

EXAMPLE

A 31.7 mg sample of [Ni(NH$_3$)$_6$]Cl$_2$ (previously analyzed and found to contain 38.2% NH$_3$) is accurately weighed into a previousy dried 121 ml borosilicate bottle. The bottle is then sealed, as at 14 in the drawing, with a silicon rubber septum and an aluminum crimp seal. The bottle is then heated in an oven at 150° C for 15 minutes during which time the color changes from purple to yellow as result of the following equation:

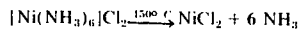

The resulting concentration of NH$_3$ in the container will be 12.1 mg./121 ml or 100 μg/ml. Therefore, each 0.1 ml aliquot withdrawn with a gas tight syringe will contain 10.0 μg of NH$_3$.

The above procedure can be followed using any of the many gas sources described herein whether they be clathrates, said complexes or decomposable salts. By the technique described in the above example, many pollutants in air may be identified as to kind and amount by using corresponding gasreleasable substances, the pollutants thus including, in addition to those mentioned heretofore, such substances as vinyl chloride, ethylene, acetylene, methyl amine, triethyl amine, among others.

From the above it can be seen that a weighed amount of a gas adduct 12 containing a known amount of gas is placed in a sealed container which has a known volume. In the drawing, the container 10 has in it material 12 of this invention and is sealed at 14. The heating that is effected may be through the use of a steam bath, a low temperature oven, an infra-red lamp, or the like. In other words, various ways of heating such as by convention, conduction, radiation, photolysis and the like may be employed to decompose or dissociate the adducts. No special heating equipment is involved and materials which require high temperatures to effect decomposition are avoided. Such materials included the inorganic bicarbonates, carbonates, nitrates and sulfites. In general, the decomposition or dissociation temperature of the adducts of this invention occurs at or below a temperature of about 200° C. Normally, the adducts used in this invention decompose or dissociate at relatively low tempertures, being in the range of about 100° C. Also, substances which decompose to give a plurality of gases or involve the possibility of yielding a plurality of gases are not used in the process or equipment of this invention. The difficulty of materials which release or may possibly release a plurality of gases upon heating is that very frequently the precise chemical composition of the gas is not known, there being no control reaction in the thermal decomposition. For example, organic azo compounds can be decomposed by heating to yield nitrogen. However, the thermal decomposition is most frequently accompanied by the production of other gases. Generally, a compound which so decomposes to produce a mixture of gases forms non-stoichiometric compounds or mixtures of gases that are difficult to certify. However, by the process of this invention it is possible to produce custombuilt gas mixtures by using a mixture of the adducts of this invention, once each has been separately analyzed and certified. For example, a mixture of a sulfur dioxideadduct with chlorocarbonylbis(triphenylphosphine) iridium(1) and silver nitrite can be used to produce a gaseous mixture of nitrogen dioxide and sulfur dioxide, the gaseous mixture being fixed in amount as to both gases and fixed as to the kind of gases. The gaseous mixture being produced in the same container can be used in a single analysis.

In the event that low concentrations are desired so that it is difficult or impossible to weight out the adduct with direct weighing, the adduct may be dissolved in a solvent to produce a stock solution of the adduct, and the solvent then can be placed into a dried container or onto or into a support through the use of a micropipette. The container can then be handled by a variety of methods to remove the solvent and any adsorbed gas by application of a modest vacuum at room temperatures such as 25° C. After that treatment, the container can be sealed and used in the procedures described above to produce a gas as a standard. In another procedure the weighed amount of the adducts used in thi invention is contained in the barrel of a gastight syringe which is then placed in a heating zone such as in an oven. The entire sample of the desired gas can then be injected into the analytical equipment. Further, the containers of this invention such as a borosilicate glass container of known volume can be sealed with a septum cap and stored at room temperature. Upon dissociation of the gas, sample aliquots can be withdrawn from the container using a gas-tight syringe, only the needle 16 of the syringe being shown in the drawing for convenience. The use of containers sealed with a serum cap or septum is preferred with its attendant easy removal of small aliquots leaving a sealed container still fixed and known as to its contents for a further test or rerun.

Since most of the gas adducts are collored materials and the substrate is of a different color, the dissociation step is most frequently accompanied by a change in color. Thus, the end point of the dissociation can be visually observed, so that one knows very readily that the entire amount of the desired gas has been produced.

From the above, it can be seen that a wide variety of compounds can be used as the gas-producing adduct. These include hexaminenickel(11)chloride and its ammonia adduct and potassium trichloro(ethylene)-platinate(11) which decomposes by the following equation to produce ethylene

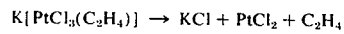

Also, an organic clathrate involving hydrogen sulfide may be used, the adduct being para-quinol hydrogen sulfide clathrate which dissociates as follows to release hydrogen sulfide:

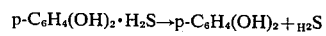

The materials and the methods used in this invention are straightforward, readily understood and require no elaborate equipment. Further, the methods of this invention are useful over a broad range of gas concentration, because one skilled in the art can use a weight of the adduct and a volume of the container over several orders of magnitude to adapt to his particular desires for and conditions of his particular analysis. The problem of adsorption or reactions of trace gases with container walls should be minimized because the containers can be properly flushed and the standard can be prepared immediately prior to its use. Still further, the standards can be prepared so that no gaseous products other than those desired are released upon the dissociation of the adduct. Since the adduct is decomposed quantitatively, as evidenced, for example, by a color change or an infra-red spectrum of the residue, the amount of gas that is in the container is not dependent upon the temperature used in its dissociation. The methods and the materials and apparatus of this invention also allow one to readily withdraw aliquots into analysis, using weight methods, and in any given analysis the operator can use whatever type of atmosphere he wishes simply by flushing the container in stream with the desired atmosphere after the solid adduct has been added. A weight range of gas concentrations can be prepared very easily as, for example, very small parts per million to a range of 1% level in any gas atmosphere. This is a distinct advantage over previous methods such as the use of permeation tubes, each of which must be individually calibrated under well-defined conditions and which tubes are inaccurate at high concentrations. If large aliquots are removed, as the standard is depleted, a correcton for the amount of gas removed can easily be applied.

The containers used in this invention may be made from a variety of materials, such as glass of various kinds with a borosilicate glass being preferred, metals, such as copper or aluminum or plastics, such as a polycarbon like polyethylene or polypropylene, or other polymeric materials including poly(tetrafluoroethylene), polyamides, the various polyvinyls, among others, the requirements for a container being that it be inert to and non-adsorptive of the chemicals involved in the standard, be easily sealed and unsealed and be impermeable. The containers are, of course, readily used in conjuction with any of the many detectors used in analytical procedures such as a chromatograph.

While the invention has been disclosed herein in connection with certain embodiments and certain structural and procedural details, it is clear that changes, modifications or equivalents can be used by those skilled in the art; accordingly, such changes within the principles of the invention are intended to be included within the scope of the claims below.

What is claimed is:

1. A method for the provision of a primary standard which method comprises:
   placing into a container of known volume a known amount of a material from which a gas may be released in a known amount by heating;
   sealing said container;
   effecting the dissociation of said gas from said material in said container by heating said material to its dissociation temperture; and
   withdrawing from said container a known amount of said gas for use in calibrating a detector.

2. A method in accordance with claim 1 in which said material releases a mixture of gases upon said heating.

3. A method in accordance with claim 1 in which said gas is released at a temperature no higher than about 200° C. and is an inorganic gas.

4. A method in accordance with claim 1 in which said gas is released at a temperature no higher than about 200° C. and is an organic gas.

5. A method in accordance with claim 1 in which said container has a known volume.

6. A method in accordance with claim 1 in which said container has in it more than one kind of the said material, thereby to produce a mixture of gases.

7. A method in accordance with claim 1 in which said sealing is effected using a septum.

8. A method in accordance with claim 7 in which an aliquot of said gas is withdrawn through said septum using a gastight syringe.

9. A method in accordance with claim 1 in which said material is a combination of a clathrate and gas.

10. A method in accordance with claim 9 in which said clathrate is an inorganic clathrate.

11. A method in accordance with claim 9 in which said clathrate is an organic clathrate.

12. A method in accordance with claim 1 in which said material is a combination of a transition metal complex and a gas.

13. A method in accordance with claim 12 in which said complex is an iridium compound.

14. A method in accordance with claim 13 in which said iridium compound is a gas adduct of chlorocarbonylbis (triphenylphosphine) iridium(1).

15. A method in accordance with claim 13 in which said iridium compound is a gas adduct of bis(1,2-diphenylphosphinoethane) iridium(1) chloride.

* * * * *

UNITED STATES PATENT OFFICE
CERTIFICATE OF CORRECTION

Patent No. 3,997,296  Dated December 14, 1976

Inventor(s) Warren V. Miller

It is certified that error appears in the above-identified patent and that said Letters Patent are hereby corrected as shown below:

Column 1, line 18, "if" should read -- of --; line 42, "tandard" should read -- standard --. Column 2, line 11, "prevously" should read -- previously --; same line 11, before "air" insert -- the --; line 58, "xuy-lenes" should read -- xylenes --. Column 3, line 47, after "decomposition" insert -- or dissociation --; line 54, after "100° C." insert -- to about 150° C. --. Column 4, line 5, "dioxideadduct" shuold read -- dioxide adduct --; line 39, "collored" should read -- colored --. Column 5, line 2, after "adsorption or" insert -- absorption --.

Signed and Sealed this

Third Day of May 1977

[SEAL]

Attest:

RUTH C. MASON
Attesting Officer

C. MARSHALL DANN
Commissioner of Patents and Trademarks